United States Patent [19]

Koenig et al.

[11] 4,065,454

[45] Dec. 27, 1977

[54] 1,3-DIDESOXY-1,3-[N,N'-(1',2',3',4'-TETRAHYDRO-1',4'-DIOXO)-PHTHALAZINO]-INOSITOL COMPOUNDS

[75] Inventors: Horst Koenig, Ludwigshafen; Horst Prinzbach; Reinhard Schwesinger, both of Freiburg, all of Germany

[73] Assignee: BASF Aktiengesellschaft, Ludwigshafen, Germany

[21] Appl. No.: 708,604

[22] Filed: July 26, 1976

[30] Foreign Application Priority Data

Aug. 11, 1975 Germany ............................ 2535754

[51] Int. Cl.$^2$ .......................................... C07D 237/30
[52] U.S. Cl. ............................ 260/250 P; 260/563 R
[58] Field of Search ...................................... 260/250 P

[56] References Cited

U.S. PATENT DOCUMENTS

| 3,894,015 | 7/1975 | Stachel et al. ................. 260/250 P |
| 3,957,776 | 5/1976 | Podesva et al. ................ 260/250 P |

Primary Examiner—Nicholas S. Rizzo
Attorney, Agent, or Firm—Keil, Thompson & Shurtleff

[57] ABSTRACT

The reaction product obtained from cis-benzenetrioxide, hydrazine and phthalic anhydride, and its manufacture. The compounds are intermediates for stereospecific syntheses of aminocyclitols.

4 Claims, No Drawings

1,3-DIDESOXY-1,3-[N,N'-(1',2',3',4'-TETRAHYDRO-1',4'-DIOXO)-PHTHALAZINO]-INOSITOL COMPOUNDS

The present invention relates to compounds of the formula (1)

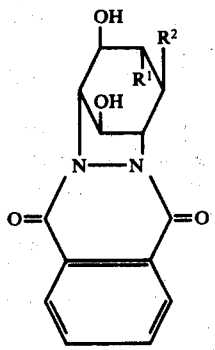

where $R^1$ and $R^2$ are each OH, or $R^1$ and $R^2$, together with the carbon atoms by which they are linked, form an epoxide ring.

In particular, the invention relates to the following compounds: DL-1,2-anhydro-4,6-didesoxy-4,6-[N,N'-(1',2',3',4'-tetrahydro-1',4'-dioxo)-phthalazino]-myo-inositol and 1,3-didesoxy-1,3-[N,N'-(1',2',3',4'-tetrahydro-1',4'-dioxo)-phthalazino]-scyllo-inositol.

In accordance with the conventional rules of nomenclature, the 1,3-position may also be referred to as the 4,6-position.

The compounds according to the invention may be manufactured from DL-1,2-anhydro-4,6-biimino-4,6-didesoxy-myo-inositol (2) by reaction with phthalic anhydride, which may or may not be followed by opening of the epoxide ring in the presence of an oxy-acid.

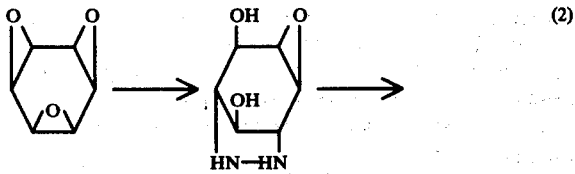

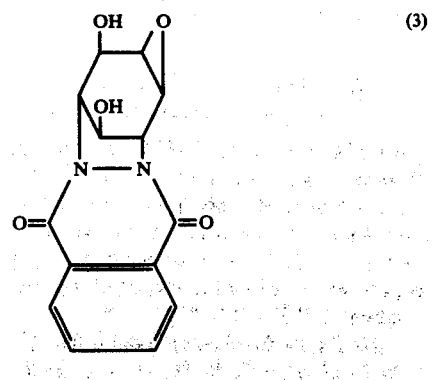

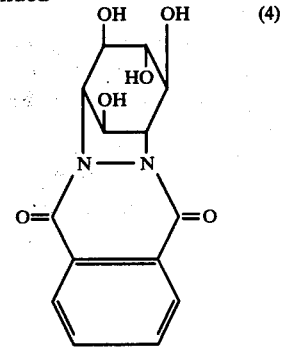

The starting compound (2) is obtained by reacting cis-benzenetrioxide with hydrazine.

In general, the procedure followed is to react the cis-benzenetrioxide with an equimolar amount or an excess, preferably a 2-molar to 4-molar amount, of hydrazine in an aqueous medium, at elevated temperatures. Solvents which may be used are not only water but also lower alcohols, e.g. methanol or ethanol, or water-alcohol mixtures. The reaction is advantageously carried out at from room temperature to 100°, preferably at from 30° to 60° C.

In a particularly advantageous embodiment, the cis-benzenetrioxide is reacted, in aqueous solution, with an 0.2–2 molar hydrazine solution in from 2.5 to 3.5 molar excess, at from 45° to 55° C. Within a period of from 10 to 100 minutes, only a part of the cis-benzenetrioxide, from about 30 to 50%, is converted, but side-reactions are avoided and a very pure compound of the formula (2) is obtained. The unconverted cis-benzenetrioxide can easily be recovered by extraction, e.g. with methylene chloride or chloroform, and can be reused without requiring special purification.

The epoxy-hydrazine compound (2) forms colorless crystals which melt, with decomposition, at 235° C. Their tetraacetyl derivative forms crystals of melting point 179.5° – 181.5° C.

For further reaction with phthalic anhydride, the epoxyhydrazine compound (2) does not require special purification. The phthalic anhydride is advantageously used in from 1 to 1.5 molar amount and the reaction is carried out in an aqueous or alcoholic medium, in particular in a methanolic medium, at an elevated temperature, preferably at from 10° to 70° C.

Where required, the epoxide ring of the resulting azinedione can advantageously be opened stereospecifically, by heating a saturated aqueous solution in the presence of catalytic amounts of an oxy-acid, to give the tetrol having the scyllo-configuration. The hydrolysis reaction is as a rule carried out at elevated temperatures, up to the boiling point of water, by conventional methods. The reaction can also be carried out advantageously in a closed system under pressure at from 120° to 200° C.

Suitable oxy-acids are inorganic and organic oxy-acids, e.g. sulfuric acid, perchloric acid, phosphoric acid, acetic acid and phthalic acid.

The preferred oxy-acid is phthalic acid, which may be used in the form of phthalic anhydride.

The tetrol having the scyllo configuration may also be obtained directly from (2), e.g. in a single-vessel reaction, if an appropriately increased amount of phthalic anhydride is used and the reaction is carried out under pressure.

The compounds according to the invention are intermediates for stereospecific syntheses of aminocyclitols, which are, e.g. constituents of aminoglycoside antibiotics.

Thus, the above compounds can, after elimination of the phthalic acid protective group and subsequent catalytic reduction, be converted to streptamine (6).

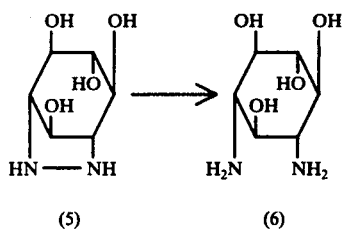

In an alkaline medium, the azinedione ring of the compound (4) can be opened, the phthalic acid eliminated and the hydrazine compound (5) liberated.

The elimination of the phthalic acid can be carried out easily and is effected in the conventional manner in 1-6 molar aqueous alkali metal hydroxide solution, preferably sodium hydroxide solution or potassium hydroxide solution, at from 50° to 100° C. As a rule, from 5 to 7 moles of alkali, based on starting compound (4), are added to the reaction mixture. At times, it is advantageous to carry out the reaction under nitrogen, with exclusion of atmospheric oxygen. The phthalic acid can also be eliminated by using hydrazine as the base.

The end point of the hydrolysis is simple to determine by NMR spectroscopy.

The hydrogenolysis of the nitrogen-nitrogen bond of the compound (5) gives streptamine. This catalytic reduction is carried out in the presence of Raney nickel or of noble metal catalysts, in particular platinum, as a rule at room temperature or elevated temperatures of up to 50° C, using hydrogen under atmospheric pressure or elevated pressures of up to 100 atmospheres. The compound (5) need not be isolated as a pure substance after eliminating the phthalic acid; instead, the reaction mixture containing alkali can be used directly. The streptamine obtained is advantageously precipitated as a sparingly soluble salt, e.g. as the sulfate, and can, if desired, be worked up as an acylated compound, preferably as the acetyl derivative, which in general is more easily isolated and more readily crystallizable.

The intermediates according to the invention provide an inexpensive method of producing streptamine in high yields. It was surprising, and unforeseeable, that the azinedione of the formula (1) could be manufactured under simple conditions, in high yield and great purity, without the occurrence of side-reactions. The azinedione ring proves to be an excellent and superior protective group, so that further reactions can be carried out on the compound. The presence of the azinedione ring is responsible for the fact that a stereospecific ring opening of the epoxide, to give the streptamine configuration, takes place.

Streptamine, and streptidine which can be manufactured therefrom, are used for the synthesis of antibiotics, and may be used, e.g., for the synthesis of dihydrostreptamycin, as described by S. Umezawa et al, in J. Amer. Chem. Soc. 96, 920/21 (1974). It is also possible to add the compound to, e.g., the nutrient media of micro-organisms which synthesize antibiotic compounds, as described, e.g., in the book "Structures and Syntheses of Aminoglycoside Antibiotics" by S. Umezawa in Advances in Carbohydrate Chemistry and Biochemistry, Vol. 30, pages 111 et seq. (1974), Academic Press, or by W. Thomas Shier et al. in Proceedings of the National Academy of Science 63, 198-204 (1969).

With the aid of mutant micro-organisms, which only produce antibiotics if certain aminocyclitols, e.g. 2-desoxystreptamine, are added to the nutrient solution, it is possible to manufacture new semi-synthetic aminoglycoside antibiotics.

Thus, e.g., using the Streptomyces fradiae mutant ATCC 21,401, and adding streptamine to the nutrient solution, the neomycin-analogous antibiotics Hybrimycin A 1 and A 2 are obtained (U.S. Pat. No. 3,669,838), whilst with the 2-desoxy-streptamine-negative mutant ATCC 14,827 of the Paromomycin-producing strain Streptomyces rimosus forma paromomycinus, addition of streptamine results in the production of the Paromomycin-analogs Hybrimycin C 1 and C 2 (Shier et al., Biochemistry 13, 5073 (1974)).

In the same way, using the 2-desoxystreptamine-negative mutant of Streptomyces ribosidificus (AF-1), the addition of streptamine results in new biologically active Ribostamycin analogs (M. Kojimy and A. Satoh, Journal of Antibiotics 26, 784 (1973)).

EXAMPLES

1.

DL-1,2-Anhydro-4,6-biimino-4,6-didesoxy-myo-inositol (2)

2.52 g (20 mmoles) of cis-benzenetrioxide are reacted with 60 ml of a molar hydrazine solution in the course of 35 minutes at 50° C. The mixture is rapidly cooled to 0° C and is extracted with seven 60 ml portions of ice-cold chloroform in order to remove uncoverted cis-benzenetrioxde. The solution is then concentrated to dryness under reduced pressure at below 30° C, finally under the vacuum from a diffusion pump. The partially crystalline residue is dissolved (or suspended) in a little absolute methanol and is left to crystallize at a low temperature (about −20° C). The product is filtered off, rinsed with a little ice-cold methanol, immediately dried under reduced pressure and recrystallized from methanol. 2.50 g (79%) of colorless crystals of melting point about 235° C are isolated. 17% of product, of adequate purity for reaction with phthalic anhydride, remain in the mother liquor.

$C_6H_{10}N_2O_3$ (158.2) Calculated: C, 45.56; H, 6.37; N, 17.71. Found: C, 45.48; H, 6.11; N, 18.24.

2.

DL-3,5-Di-O-acetyl-4,6-(N,N'-diacetylbiimino)-1,2-anhydro-4,6-didesoxy-myo-inositol.

0.79 g (5 mmoles) of DL-1,2-anhydro-4,6-biimino-4,6-didesoxy-myo-inositol are dissolved in 5 ml of pyridine and 5 ml of acetic anhydride, the solution is left for 4 days at 20° C and the excess reagent is removed in vacuo. The residue is recrystallized from methanol. 1.6 g (98% ) of colorless crystals are obtained; melting point 179.5° − 181.5° C.

$C_{14}H_{18}N_2O_7$ (326.3) Calculated: C, 51.53; H, 5.56; N, 8.59. Found: C, 51.79; H, 5.50; N, 8.72.

3. DL-1,2-Anhydro-4,6-didesoxy-4,6-[N,N'-(1',2',3',4'-tetrahydro-1',4'-dioxo)-phthalazino]-myo-inositol (3).

1.58 g (10 mmoles) of DL-1,2-anhydro-4,6-biimino-4,6-didesoxy-myo-inositol are stirred with 1.63 g (11 mmoles) of finely powdered phthalic anhydride in 20 ml of water, until reaction is complete. The mixture is then briefly heated to 50° C and the product is filtered off and rinsed first with water and then with methanol. 2.80 g (97%) of colorless crystals, of melting point about 285° C (with decompositon) are obtained.

$C_{14}H_{12}N_2O_5$ (288.3) Calculated: C, 58.33; H, 4.20; N, 9.72. Found: C, 58.00; H, 4.64; N, 10.04.

IR (KBr): 3,508, 3,350 (OH), 3,075, 3,040 (CH) Abb., 1,664, 1,626, 1,604 (C=O, C=C), 1,475, 1,433, 1,396, 1,302, 1,244 (epoxide), 1,172, 1,114, 1,070, 1,022, 951, 893, 869, 798, 766, 723, 700, 487, 378 and 342 $cm^{-1}$.

$^1$H-NMR ($D_6$-DMSO): $\tau$ = 1.75–2.25 (M, 4H), 4.73 (t, 1H), 5.2–5.8 (m, 3H), 6.14 (t, 1H), 6.44 (t, 1H).

4. 1,3-Didesoxy-1,3-[N,N'-(1',2',3',4'-tetrahydro-1',4'-dioxo)-phthalazino]-scyllo-inositol (4).

a. 2.88 g (10 mmoles of DL-1,2-anhydro-4,6-didesoxy-4,6-[N,N'-(1',2',3',4'-tetrahydro-1',4'-phthalazino]-myo-inositol and 0.3 g of phthalic anhydride in 10 ml of water are heated under pressure for 20 hours at 170° C. On cooling, a hydrate of phthalazine crystallizes out. The crude product can be purified by recrystallization from water, using active charcoal, and can be obtained in an analytically pure form by drying under reduced pressure at 150° C. 3.00 g (98%) of colorless crystals of melting point about 297° C (with decomposition) are obtained.

$C_{14}H_{14}N_2O_6$ (306.3) Calculated: C, 54.90; H, 4.61; N, 9.15. Found: C, 54.86; H, 4.75; N, 9.25.

IR (KBr): about 3,300 (OH), 2,920 (CH), 1,629, 1,605 Abb. (C=O, C=C), 1,476, 1,400, 1,362, 1,305, 1,229, 1,127, 1,058, 807, 732, 700 and 376 $cm^{-1}$.

$^1$H-NMR ($D_6$-DMSO): $\tau$ = 1.9–2.27 (m, 4H), 5.3 (br.s), 6.04 (br.s).

b. The same compound can be obtained in about the same yield if, under the same conditions, 1.58 g (10 mmoles) of 4,6-biimino-4,6-didesoxy-myo-inositol (2) are reacted with 1.78 g of phthalic anhydride.

5. Streptamine sulfate (6)

3.06 g (10 mmoles) of phthalazinedione (4) and 10 ml of 5 molar sodium hydroxide solution are heated for 6 hours at 100° C under a stream of nitrogen. The product is then hydrogenated with hydrogen in the presence of Raney Ni at 20° C/10 atmospheres for 24 hours. The catalyst is filtered off, the solution is purified with active charcoal and acidified with sulfuric acid, and after adding methanol the product is allowed to crystallize. It is filtered off and washed with 50 percent strength aqueous methanol and then with pure methanol. 1.93 g (70%) are isolated; for identification, a sample was converted into streptamine hexaacetate by the method described in the literature (R. L. Peck et al., J. Amer. Chem. Soc. 69, 776 (1946)), and its melting properties, $^1$H-NMR spectrum and IR spectrum were compared with an authentic sample.

We claim:
1. A compound of the formula 1

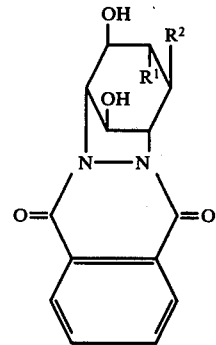

where $R^1$ and $R^2$ are each OH or $R^1$ and $R^2$, together with the carbon atoms by which they are linked, form an epoxide ring.

2. DL-1,2-Anhydro-4,6-didesoxy-4,6-[N,N'-(1',2',3',4'-tetrahydro-1',4'-dioxo)-phthalazino]-myo-inositol.

3. 1,3-Didesoxy-1,3-[N,N'-(1',2',3',4'-tetrahydro-1',4'-dioxo)-phthalazino]-scyllo-inositol.

4. A process for the manufacture of compounds of the formula

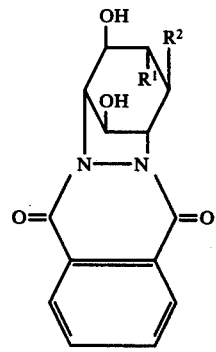

wherein the reaction product of cis-benzenetrioxide and hydrazine is reacted with phthalic anhydride used in from 1 to 1.5 molar amount in an aqueous or methanolic medium at temperatures of from 10° to 70° C, and, if required, the epoxide ring which remains is opened at elevated temperatures and in the presence of an oxyacid selected from the group consisting of the sulfuric acid, perchloric acid, phosphoric acid, acetic acid and phthalic acid.

* * * * *